United States Patent
Rees et al.

(10) Patent No.: US 8,298,482 B2
(45) Date of Patent: *Oct. 30, 2012

(54) VAPOR PHASE HYDROGEN PEROXIDE DEODORIZER

(75) Inventors: Wayne M. Rees, Racine, WI (US); Julie A. Whitcomb, Menomonee Falls, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 308 days.

This patent is subject to a terminal disclaimer.

(21) Appl. No.: 12/659,868

(22) Filed: Mar. 24, 2010

(65) Prior Publication Data

US 2010/0215540 A1    Aug. 26, 2010

Related U.S. Application Data

(63) Continuation-in-part of application No. 11/149,360, filed on Jun. 10, 2005, now abandoned.

(51) Int. Cl.
  *A61L 9/00* (2006.01)
  *A62B 7/08* (2006.01)
(52) U.S. Cl. ............... 422/5; 422/4; 422/120; 422/122; 422/123
(58) Field of Classification Search ............ 422/5, 120, 422/122, 123, 4
  See application file for complete search history.

(56) References Cited

U.S. PATENT DOCUMENTS

| | | |
|---|---|---|
| 4,036,994 A | 7/1977 | Ear |
| 4,107,268 A | 8/1978 | O'Neill et al. |
| 4,550,010 A | 10/1985 | Chelu |
| 4,909,999 A | 3/1990 | Cummings et al. |
| 5,071,622 A | 12/1991 | Dunson, Jr. |
| 5,137,687 A | 8/1992 | Dunson, Jr. |
| 5,207,877 A | 5/1993 | Weinberg et al. |
| 5,258,162 A | 11/1993 | Andersson et al. |
| 5,770,739 A | 6/1998 | Lin et al. |
| 5,779,973 A | 7/1998 | Edwards et al. |
| 5,904,901 A | 5/1999 | Shimono et al. |
| 6,039,922 A | 3/2000 | Swank et al. |
| 6,055,679 A | 5/2000 | Goelz et al. |
| 6,056,918 A | 5/2000 | Palaniappan et al. |
| 6,094,887 A | 8/2000 | Swank et al. |
| 6,183,691 B1 | 2/2001 | Swank et al. |
| 6,365,099 B1 | 4/2002 | Castrantas et al. |
| 6,495,096 B1 | 12/2002 | Hamaguchi et al. |
| 6,815,408 B2 | 11/2004 | Wegner |
| 7,670,565 B2 | 3/2010 | McVey et al. |
| 2004/0182793 A1 | 9/2004 | Owens |

FOREIGN PATENT DOCUMENTS

| | | |
|---|---|---|
| EP | 0 164 818 A2 | 12/1985 |
| EP | 0 164 818 A3 | 12/1985 |
| EP | 1 029 552 A1 | 8/2000 |
| EP | 1 393 629 A1 | 3/2004 |
| WO | WO 94/11091 A1 | 5/1994 |
| WO | WO 99/08932 A1 | 2/1999 |
| WO | WO 2004/035718 A2 | 4/2004 |
| WO | WO 2004/035718 A3 | 4/2004 |

*Primary Examiner* — Regina M. Yoo

(57) ABSTRACT

Compositions and methods for reducing or eliminating malodors from air and surfaces in contact with air within indoor environments are described. One method provided is for the reduction or elimination of malodors from air and surfaces in contact with air within an indoor environment using hydrogen peroxide in the vapor phase generated and passively emitted from pH neutral to mildly acidic aqueous-based liquid compositions. A second method is provided for the reduction or elimination of malodors from air and surfaces in contact with air within an indoor environment using hydrogen peroxide in the vapor phase as sublimed from solid compositions containing at least one pH neutral to mildly acidic solid hydrogen peroxide-containing compound.

12 Claims, No Drawings

VAPOR PHASE HYDROGEN PEROXIDE DEODORIZER

CROSS REFERENCE TO RELATED APPLICATION

This application is a continuation-in-part application of U.S. Ser. No. 11/149,360 filed Jun. 10, 2005 now abandoned.

FIELD OF THE INVENTION

This invention relates to odor reduction or elimination from air and surfaces in contact with air in indoor environments through the generation and emission of hydrogen peroxide in the vapor phase into the air. Specifically, the invention relates to compositions and methods by which odor reduction or elimination is accomplished using vapor phase hydrogen peroxide. More specifically, the invention relates to methods by which odors, such as smoke, are reduced or eliminated by the generation and emission of hydrogen peroxide in the vapor phase from pH neutral to mildly acidic aqueous compositions or solid compositions containing at least one pH neutral to mildly acidic hydrogen peroxide-containing compound.

BACKGROUND OF THE INVENTION

Malodorous substances can be present in or on a variety of media or surfaces. Individuals can be highly aware of malodors on indoor surfaces and contained in indoor air, since there is generally limited air exchange and circulation in the indoor environment in comparison to the outdoor environment. Furthermore, olfactory detection of certain malodors in many indoor settings, such as residential homes, hotels, automobile interiors, hospitals, and office buildings may give rise to a perception that the indoor area is unsanitary or soiled. Other odors, such as those originating from certain foods, cooking activities, and burned tobacco products, while not generally thought of as unsanitary or dirty, can be regarded as unpleasant by many people. Thus, there exists a need for effective removal of malodors which reside on indoor surfaces or are contained within the indoor air space. This is particularly true for cigarette smoke malodor in the air or on fabrics such as furniture, window coverings and floor coverings.

Many products are sold which are designed to remove malodors from the indoor environment. For surface deodorization, this may be accomplished through the physical removal of a malodorous substance by cleaning (detersive) activities. Malodors present in indoor air can be removed using forced air fans combined with physical absorbents, or electrical devices which employ electrostatic deposition technologies. Reactive chemistries, such as oxidizing agents, which react with and transform a malodorous substance into one or more non-odorous substances can also be employed for malodor reduction/elimination applications.

Hydrogen peroxide, an inexpensive and somewhat reactive oxidant, has found application in the area of malodor elimination or reduction. However, such uses have generally been, among other things, complex systems, expensive compositions, and/or can stand improvement. For example, U.S. Pat. No. 4,036,994 discloses the use of aqueous hydrogen peroxide solutions to remove cooked food and smoke odors from the restaurant broiling grill emissions, in part through scrubbing of the grill exhaust gas stream with these solutions. The malodor elimination process described in this patent requires cooking foods over thin, high temperature ceramic briquets to enhance incineration of potential malodors, as well as scrubbing the grill exhaust gas stream with an aqueous hydrogen peroxide solution, followed by mixing the treated gas with ambient air prior to discharge to the atmosphere.

U.S. Pat. No. 4,550,010 discloses a process for deodorizing malodors in polluted air whereby the malodorous air is washed with an aqueous solution containing both hydrogen peroxide and ozone. Similarly, U.S. Pat. No. 5,904,901 discloses removal of odors from indoor environments using an apparatus which generates and discharges both ozone and an atomized hydrogen peroxide solution, whereby reaction between ozone and atomized hydrogen peroxide generates hydroxyl radical and is said to decompose various malodorous substances present in the indoor environment.

U.S. Pat. Nos. 5,071,622 and 5,137,687 disclose processes by which malodorous substances are removed from sewage treatment systems that emit odors. In the processes, odor abatement is obtained by contacting hydrophobic components of an odor-containing gas plume condensate with odor-trapping core particles containing precipitates resulting from reaction of ferrous ion, tannic acid, and hydrogen peroxide.

U.S. Pat. Nos. 6,365,099 B1 and 6,495,096 B1 disclose processes and systems by which malodorous reduced sulfur compounds are removed from liquid waste streams associated with sewage collection/treatment. The '096 patent describes a treatment process which utilizes aqueous deodorant compositions containing hydrogen peroxide and nitrate ion or hydrogen peroxide, nitrate ion, and a transition metal salt. The aqueous deodorant compositions of the '096 patent are mixed directly with the waste stream. The '099 patent describes a process and system by which sulfide odors are reduced or eliminated from the vapor spaces of waste handling and treatment systems by injecting a fine spray, mist or fog of an aqueous alkaline hydrogen peroxide solution into air spaces within sewage-containing system handling or treatment equipment such as sewage conduits, sewers, trunk lines, and other such structures.

U.S. Pat. No. 6,815,408 B2 discloses aqueous alkaline phosphate-containing hydrogen peroxide compositions for various odor elimination and disinfection uses. The aqueous compositions are introduced onto surfaces and into air handling ducts by the application of a spray or mist of the aqueous alkaline peroxide solutions. U.S. Pat. No. 6,815,408 B2 teaches criticality in the inclusion of alkaline phosphate agents in the aqueous liquid phase peroxide solutions both as a peroxide stabilizer and an oxidation accelerator/enhancer. U.S. Pat. No. 6,815,408 B2 teaches the deodorizing action as only associated with liquid phase alkaline solutions of hydrogen peroxide. Application of these compositions to malodorous surfaces is said to concentrate the alkaline peroxide in the aqueous phase, thus enhancing deodorization activity. The pH and non-volatile alkaline agents are central to the described invention. The teachings of U.S. Pat. No. 6,815,408 B2 do not extend to or infer reactions of hydrogen peroxide in the vapor state, as pH and non-volatile alkaline materials have no applicability to the vapor state.

WO 94/11091 discloses a catalytic process for removal of odors from industrial gas streams by scrubbing such gas streams through a fixed bed scrubber fitted with a solid packing bed containing a transition metal catalyst and a hydrogen peroxide-containing liquor.

Accordingly, there is a need for compositions and methods which are generally simple and inexpensive to manufacture and provide effective reduction or elimination of malodors, particularly cigarette smoke, from indoor air spaces and surfaces.

BRIEF SUMMARY OF THE INVENTION

Indoor environments such as residential homes, hotels, automobile interiors, hospitals, and office buildings may experience unpleasant odors in their air space. Similarly, solid surfaces in such locations may also be soiled with malodorous substances. While in some cases, the malodors may be removed by simply "airing out" the location using enhanced air exchange/circulation, in other instances it may be desirable or necessary to remove such malodors using chemical treatment of the air space or surfaces. In addition, it may be desirable to provide such air spaces or surfaces with continuous long-term chemical deodorizing treatments for a period of days, weeks, or months.

In many indoor locations it is impractical or impossible to remove human or other living occupants in the event of continuous long-term chemical deodorizing treatments. When this is the case, the chemical treatments employed must not present any significant negative toxicological or hedonic concerns for the occupants. For example, ozone gas is known to effectively react with and eliminate many types of malodors. However, ozone may be regarded as a hazardous indoor air pollutant, and exposure to ozone in indoor air is strictly regulated by the U.S. Environmental Protection Agency ("EPA") for many indoor environments. Similarly, chlorine dioxide gas can be employed as a reactive malodor-eliminating reagent. Like ozone, exposure to chlorine dioxide is of significant toxicological concern and the EPA has established very low permissible exposure limits to this substance. Also, chlorine dioxide has a very low human odor detection threshold and many individuals tend to find the odor of chlorine dioxide objectionable well below the established EPA airborne exposure limits.

The present invention provides for compositions and methods of reducing or eliminating malodors from indoor air and from surfaces in contact with air located within indoor environments. The invention has been found to be particularly useful in reducing or eliminating cigarette odors from such environments.

In a first embodiment, a method of the invention provides for the elimination or reduction of malodors from air and surfaces in contact with air within an indoor environment by the use of hydrogen peroxide present in vapor phase which is generated and passively emitted, i.e., release of active hydrogen peroxide itself, from pH neutral to mildly acidic aqueous-based liquid compositions. The release of the active, hydrogen peroxide is not dependent upon and occurs independently of evaporation of the aqueous carrier of the liquid composition. Preferably, the aqueous-based liquid compositions contain no more than about 8% hydrogen peroxide by weight. The terms "passively emitted" or "passive emission" means that the active hydrogen peroxide in vapor phase is slowly generated over an extended period of time in itself and released directly in itself from a bulk aqueous composition. This excludes processes whereby the aqueous compositions are physically dispersed into the indoor air, or applied directly to indoor surfaces as bulk liquid or liquid droplets using mechanical means such as pouring, spraying, misting, fogging, or atomizing via manually operated or powered devices. In these excluded processes, the hydrogen peroxide present is dispersed in conjunction with the liquid phase of the composition. Such processes disperse considerable liquid into the air where it then deposits on surfaces, or where liquid is directly applied onto surfaces, rendering the appearance and/or feel of the surfaces undesirably wet. The pH range of the liquid hydrogen peroxide composition is preferably in the range of about pH 8 to about pH 1 in the temperature range of about 15-30° C. The pH neutral to mildly acidic aqueous-based liquid compositions may comprise low viscosity fluids, viscous gels, or thick suspensions, and may also include other ingredients including fragrance/perfume ingredients.

In another embodiment of the present invention, a method is provided for the elimination or reduction of malodors from air and surfaces in contact with air within an indoor environment using hydrogen peroxide present in the vapor phase as generated by sublimation of the active hydrogen peroxide from a solid composition containing at least one pH neutral to mildly acidic solid hydrogen peroxide-containing peroxohydrate compound. The term "sublimation" refers to a process by which hydrogen peroxide vapor is directly released from the hydrogen peroxide-containing solid in the vapor phase. No liquid phase is present in the emission from the solid composition. The terms "pH neutral to slightly acidic hydrogen peroxide-containing peroxohydrate compound" refers to a compound containing molecular hydrogen peroxide wherein the pH of a concentrated solution of the compound in purified water is less than about pH 8 in the temperature range of about 20-25° C. Examples of suitable mildly acidic hydrogen peroxide-containing peroxohydrate compounds include urea peroxohydrate, $CO(NH_2)_2 \cdot H_2O_2$; sodium sulfate peroxohydrate, $2Na_2SO_4 \cdot H_2O_2 \cdot 2H_2O$; and a peroxohydrate of poly(vinyl pyrrolidone) polymer, $PVP \cdot xH_2O_2$. The solid composition containing one or more peroxide-containing compounds may also include one or more non-peroxide containing solids, such as inert inorganic salts or solid organic compound fillers. The solid may comprise a powder, compressed tablet, crystalline solid, or other readily recognizable solid forms. The solid compositions may also include minor amounts of liquid or solid fragrance/perfume ingredients.

The foregoing and other advantages and features of the present invention will be further apparent and understood upon consideration of the following detailed description and the claims which cover the scope of the invention.

DETAILED DESCRIPTION OF THE INVENTION

Hydrogen peroxide in its pure form is a clear, colorless liquid having a slightly sharp acrid odor and a freezing point of −0.4° C. Pure liquid hydrogen peroxide exhibits a vapor pressure of ca. 2.0 mm Hg at 25° C., somewhat less than that of water (ca. 24 mm Hg at 25° C.). Aqueous solutions of hydrogen peroxide exhibit a mixed vapor phase composition of water vapor and vapor phase hydrogen peroxide, as expected for a mixture of two miscible volatile liquids. See, for example, "Hydrogen Peroxide" in Kirk-Othmer Encyclopedia of Chemical Technology, $4^{th}$ Edition, Volume 13, 1995, Wiley-Interscience Publication, and references therein.

Inorganic and organic compounds containing molecular hydrogen peroxide as solid/crystalline adducts are referred to as peroxohydrates or perhydrates. Many such materials are known in the commercial and technical literature, including such materials as sodium carbonate peroxohydrate $2Na_2CO_3 \cdot 3H_2O_2$ (sodium percarbonate); ammonium carbonate peroxohydrate, $(NH_4)_2CO_3 \cdot H_2O_2$; urea peroxohydrate, $CO(NH_2)_2 \cdot H_2O_2$ (urea peroxide); sodium sulfate peroxohydrate, $2Na_2SO_4 \cdot H_2O_2 \cdot 2H_2O$; and various peroxohydrate phosphate salts. Descriptions of various peroxohydrates can be found in "Hydrogen Peroxide, Peroxohydrates", Kirk-Othmer Encyclopedia of Chemical Technology, $4^{th}$ Edition, Volume 13, 1995, Wiley-Interscience Publication, and references therein. A polymer-containing peroxohydrate of poly(vinyl pyrrolidone), $PVP \cdot xH_2O_2$, where the hydrogen peroxide content of the compound is variable up to about 22% by weight of the composition, is commercially available as Peroxydone® from the ISP Corporation, Wayne, N.J., USA.

As to a first embodiment, we have found that aqueous liquid compositions containing hydrogen peroxide, wherein the pH of the solution is about 8 or below, can generate and passively emit into the surrounding atmosphere of an indoor environment useful amounts of active hydrogen peroxide in the vapor phase which has utility toward the elimination or reduction of malodors from the air space and surfaces surrounded by the air space of the indoor environment. Alkaline aqueous hydrogen peroxide solutions are not stable with respect to disproportionation to water and oxygen gas. Therefore, it is desirable to utilize pH neutral to mildly acidic aqueous hydrogen peroxide compositions in the pH range of about 1 to about 8. This provides acceptable long-term stability of the aqueous hydrogen peroxide-containing composition. More preferably, the pH of the liquid composition is in the range of about 2 to about 7. Most preferably, the pH of the liquid composition is in the range of about 3 to about 6, providing for optimal product stability.

The methods of the present invention are directed to the passive emission of hydrogen peroxide into indoor air space. "Passive emission," as used herein, means that active hydrogen peroxide in vapor phase is slowly generated in itself over an extended period of time and is itself released directly from a bulk aqueous composition. This excludes processes whereby the aqueous (liquid phase) compositions are dispersed into the indoor air, or applied directly to indoor surfaces as bulk liquid or as liquid droplets using mechanical means such as pouring, spraying, misting, fogging, or atomizing via manually operated or powered devices. Such excluded processes which physically disperse the hydrogen peroxide in conjunction with all components of the aqueous (liquid) of the composition, rather than strictly dispersing the active hydrogen peroxide in the gas phase itself. Thus, in the former process, the aqueous phase containing the hydrogen peroxide is at least in part dispersed by physical means (e.g., pouring, spraying, misting, etc.) and falls out of the air onto a malodorous surface or is directly applied to such surface. In the latter process, the only means of dispersing the hydrogen peroxide for the purpose of deodorization is via passive generation of gas phase hydrogen peroxide in the air to the extent such is carried into the air via the evaporation from the source (bulk solution). The aqueous pH neutral to mildly acidic aqueous hydrogen peroxide compositions of the invention may be homogeneous solutions or heterogeneous dispersions containing suspended solids. The viscosity of the liquid hydrogen peroxide compositions may range from that of a "water-thin" fluid (less than about 10 centipoise at 25° C.) to that of a highly viscous, rigid gel, paste or suspension (about 100,000 cps or greater at 25° C.) Viscosity building agents may include peroxide-stable surfactant systems, peroxide-stable polymers, as well as various solid inorganic thickening agents/fillers such as alumina, silica, and natural/synthetic clays.

The concentration of hydrogen peroxide in the aqueous compositions may comprise up to about 50% by weight of the composition, preferably less than about 10% by weight of the composition and most preferably about 8% to about 0.5% by weight of the composition. The aqueous compositions may include minor amounts of other ingredients, including fragrance ingredients and fragrance solubilizing agents such as surfactants or solvents, and/or colorant(s) for aesthetic purposes. For optimal stability, the aqueous compositions may also include one or more hydrogen peroxide-stabilizing agents, such as, for example, stannate compounds, phosphate salts, organophosphonates, and various chelating agents derived from aminocarboxylates or aminophosphonates. Various peroxide-stabilizing agents are disclosed in "Hydrogen Peroxide, Stabilization", Kirk-Othmer Encyclopedia of Chemical Technology, $4^{th}$ Edition, Volume 13, 1995, Wiley-Interscience Publication and the references therein, incorporated herein by reference. Additional ingredients may include peroxide-stable acids for pH adjustment, including but not limited, to sulfuric acid, phosphoric acid, sulfamic acid, acetic acid, propanoic acid, citric acid, adipic acid, glutaric acid, succinic acid, and polyacrylic acid.

Various dispensing devices are suitable for malodor reduction or elimination applications using passive generation and emission of vapor phase hydrogen peroxide from low viscosity aqueous hydrogen peroxide-containing solutions. Liquid wicking devices, such as container-dispensing systems for liquid air fresheners, are especially useful. Container-dispensing devices suitable for the methods and compositions of the present invention disclosed herein include those set forth in U.S. Pat. Nos. 2,802,695; 3,550,853; 4,286,754; 4,413,779; 4,913,350; 5,000,383; 5,014,913; 5,121,881; 5,749,519; 5,749,520; 5,875,968 and 6,871,794 B2, incorporated herein by reference. Materials of construction for such devices are selected so as to provide for the integrity of the container-dispenser with respect to the oxidizing and corrosive nature of the aqueous hydrogen peroxide solutions described in the present invention.

Viscous gels or suspensions of the present invention may be contained within dish or cup type containers, having at least one opening so as to permit the passive emission of the hydrogen peroxide-containing composition, producing a suitable concentration of vapor phase hydrogen peroxide in the indoor air space. Examples of suitable containers include those disclosed in U.S. Design Pat. Nos. 295,675; 307,469; 332,999; and 376,002, incorporated herein by reference.

Various mechanical devices may be utilized in combination with hydrogen peroxide-containing viscous gels or suspensions of the present invention. These devices include those which will enhance effective generation of vapor phase hydrogen peroxide within the indoor environments by utilizing mild heating of the inventive compositions, which are enclosed within appropriate containers. Such heating devices, used to promote the dispensing of volatile liquid compositions, include those disclosed in U.S. Pat. Nos. 3,633,881; 4,020,321; 4,968,487; 5,038,394; 5,290,546; 5,647,053; 5,903,710; 5,945,094; 5,976,503; 6,123,935; and 6,862,403 B2, incorporated herein by reference. Fan type devices may also be employed to enhance the generation of vapor phase hydrogen peroxide within the indoor environments by flowing a stream of air across the inventive compositions, which are enclosed within appropriate containers. Such fan type devices, used to promote the dispensing of volatile liquid compositions, include those disclosed in U.S. Pat. Nos. 4,840,770; 5,370,829; 5,547,616; 6,361,752 B1 and 6,371,450 B1, incorporated herein by reference.

In a second embodiment of the invention, we have surprisingly found that certain solid peroxyhydrate compounds, when exposed to ambient indoor air, will liberate useful amounts of hydrogen peroxide in the vapor phase with utility towards reduction or elimination of malodors from the air space and surfaces in the air space of an indoor environment. These peroxyhydrate compounds may comprise part, or all, of solid compositions which sublime hydrogen peroxide direct from the solid composition into the vapor phase at ambient room temperatures, i.e., no liquid phase is present in the sublimation of the hydrogen peroxide. The amount of peroxyhydrate utilized in the solid composition will depend on the hydrogen peroxide content of the peroxohydrate and the release rate of hydrogen peroxide vapor from a given peroxohydrate, relative to the desired rate of release for the composition containing the peroxohydrate. Ambient indoor air generally contains a significant amount of water vapor, and alkaline peroxohydrate compounds are unstable with respect to disproportionation to water and oxygen gas upon exposure to water vapor. Thus, it is necessary to utilize pH neutral to slightly acidic peroxohydrate compounds. The terms "pH neutral to slightly acidic peroxohydrate compound" refers to a peroxohydrate compound wherein the pH of a concentrated (ca. 5% by weight in water) solution of the compound in purified water is less than about pH 8 in the temperature range of about 20-25° C.

Examples of suitable mildly acidic hydrogen peroxide-containing peroxohydrate compounds include urea peroxohydrate, $CO(NH_2)_2.H_2O_2$; sodium sulfate peroxohydrate, $2Na_2SO_4.H_2O_2.2H_2O$, and a peroxohydrate of poly(vinyl pyrrolidone) polymer, $PVP.H_2O_2$, where the hydrogen peroxide content of the polymeric PVP peroxohydrate can range up to about 22% by weight. The solid composition containing one or more peroxide-containing peroxohydrate compounds may also include one or more non-peroxide containing filler solids, such as inert inorganic salts or solid organic compounds. Examples of inert fillers include alkali metal sulfate salts, alkaline earth sulfate salts, silica, alumina, and talc.

The solid composition may comprise a powder, compressed tablet, crystalline solid, or other readily recognizable solid forms. The hydrogen peroxide content of the solid composition can be as high as about 50% by weight hydrogen peroxide, but preferably about 25% by weight or less for reasons of, among other things, product processing and stability. More preferably, the solid compositions have a hydrogen peroxide content in the range of about 0.1% to about 10% by weight. Most preferably, the solid compositions have a hydrogen peroxide content in the range of about 0.5% to about 8% by weight.

The solid composition may include minor amounts of other ingredients, including fragrance ingredients, and/or colorant(s) for aesthetic purposes. Minor amount of other ingredients, such as surfactants, solvents, and processing aids, (e.g., anticaking agents, mold release agents, shape-forming agents or binders, etc.) may also be included in the solid compositions of the present invention. For optimal peroxide stability, the compositions of the present invention may also include one or more hydrogen peroxide-stabilizing agents, such as stannate compounds, phosphate salts, organophosphonates, and various chelating agents derived from aminocarboxylates or aminophosphonates. Various peroxide-stabilizing agents are disclosed in "Hydrogen Peroxide, Stabilization", Kirk-Othmer Encyclopedia of Chemical Technology, $4^{th}$ Edition, Volume 13, 1995, Wiley-Interscience Publication, and references therein, and incorporated herein by reference.

The solid hydrogen-peroxide-containing compositions of this invention may be packaged within various types of containers which permit the sublimation of vapor phase hydrogen peroxide into indoor air space. These packages include pouches or bags, which allow for the transmission of hydrogen peroxide vapor through the package walls. The solid compositions may also be contained within a cup or dish having one or more suitable openings which permit vapor phase hydrogen peroxide transmission from within the container into the indoor air space. If the solid hydrogen-peroxide-containing compositions are of a powdered, granule, or particulate form, a container such as a dish or cup may include a physical barrier preventing the solid from being discharged from the container by shaking, inverting, or the like. Appropriate physical barriers include a covering of fabric or screen-type material of sufficiently small pore/mesh size, such that the solid powder or particulate can not pass though the fabric/screen, however the pores in the covering will allow for the transmission of hydrogen peroxide in the vapor phase into the indoor air space.

Various mechanical devices may be utilized in combination with hydrogen peroxide-containing solid compositions of the present invention. These devices include those which will enhance effective generation of vapor phase hydrogen peroxide within the indoor environments by utilizing mild heating of the inventive compositions, which are enclosed within appropriate containers. Such heating devices, used to promote the dispensing of volatile compositions, include those disclosed in U.S. Pat. Nos. 3,633,881; 4,020,321; 4,968,487; 5,038,394; 5,290,546; 5,647,053; 5,903,710; 5,945,094; 5,976,503; 6,123,935; and 6,862,403 B2, incorporated herein by reference. Fan type devices may also be employed to enhance the generation of vapor phase hydrogen peroxide within the indoor environments by flowing a stream of air across the inventive compositions, which are enclosed within appropriate containers. Such fan type devices, used to promote the dispensing of volatile compositions, include those disclosed in U.S. Pat. Nos. 4,840,770; 5,370,829; 5,547,616; 6,361,752 B1 and 6,371,450 B1, incorporated herein by reference.

Solid compositions of the present invention may also be employed in the form of a powder or other solid particulate, to be purposefully dispensed for example, by shaking, from a container for application to household surfaces such as carpet or upholstery.

Solid hydrogen peroxide-containing compositions of this invention may also be molded into single-piece articles including a tablet, disk, puck, cube, ball, or other appropriate shape. In this case, the matrix and surface area of the solid article are designed to allow for effective transmission of hydrogen peroxide through the bulk composition with sublimation of hydrogen peroxide vapor from the surface of the article.

We have found that low concentrations of hydrogen peroxide in the vapor phase contained within an indoor air environment, either generated and passively emitted from pH neutral to mildly acidic aqueous liquid compositions containing hydrogen peroxide, or sublimed from solid compositions containing at least one pH neutral to mildly acidic solid hydrogen peroxide-containing peroxohydrate compound, have utility towards reduction or elimination of malodors from the air space and surfaces in contact with the air space in an indoor environment. In particular, we have found such compositions and methods to be useful for the reduction or elimination of tobacco smoke odors from textiles, fabrics (such as clothing, furniture coverings, carpets, window treatments, etc.), and other indoor surfaces, and for the reduction or elimination of various other malodors, especially those containing reduced sulfur and nitrogen compounds, from both the air space and various surfaces in contact therewith in indoor environments.

The following examples are set forth to illustrate the utility of the compositions and methods of the present invention towards the reduction or elimination of malodors from indoor surfaces and indoor air spaces. These examples are not intended to limit the scope of the invention.

EXAMPLE 1

Generation of Hydrogen Peroxide in the Vapor Phase from Aqueous Liquid Hydrogen Peroxide Compositions Three 50 gram samples of liquid aqueous hydrogen peroxide-containing compositions as set forth in Table 1 were placed in individual 66 liter polypropylene test chambers, maintained at 23° C. The amounts of hydrogen peroxide concentrations in the vapor phase inside the test chambers were quantified over extended periods of time using a Draeger Pac III® gas monitor, fitted with a hydrogen peroxide sensor from Draeger Safety, Inc., Pittsburgh, Pa., USA. The hydrogen peroxide generated in the vapor phase is expressed in units of ppm and is set forth in Table 2.

TABLE 1

Aqueous Acidic Hydrogen Peroxide Compositions 1, 2, 3

| Ingredient | Composition 1 | Composition 2 | Composition 3 |
|---|---|---|---|
| Hydrogen peroxide | 8.0% | 8.0% | 8.0% |
| Fumed silica | — | 8.0% | — |
| Urethane gel | — | — | 5% |
| Glycerol | — | 12.5% | — |
| Tripropylene glycol butyl ether | — | 2.5% | — |
| Dequest 2010[+] | — | 0.05% | — |
| Dowfax 2A1[++] | — | 0.25% | — |
| Fragrance | — | 0.5% | 0.5% |
| DI Water | To 100% | To 100% | To 100% |
| pH | 4.5 | 2.5 | 5.3 |

[+]Dequest 2010 = 1-hydroxyethylidene-1,1-phosphonic acid, 60% active in water. Solutia, Inc., St. Louis, MO, USA.
[++]Dowfax 2A1 = Benzene, 1,1-oxybis-tetrapropylene derivatives, sulfonated Na salts, 45% actives in water. Dow Chemical Company, Midland, MI, USA.

TABLE 2

Generation of Hydrogen Peroxide In The Vapor Phase From Aqueous Liquid Hydrogen Peroxide Compositions of Table 1

| Time (minutes) | Composition 1 | Composition 2 | Composition 3 |
|---|---|---|---|
| 0 | 0.0 ppm | 0.0 ppm | 0.0 ppm |
| 10 | 0.2 | 6.7 | 0.8 |
| 40 | 0.7 | 10.4 | Not determined |
| 60 | 0.9 | 12.7 | 1.8 |
| 300 | 1.5 | 11.8 | 6.0 |

EXAMPLE 2

Generation of Hydrogen Peroxide in the Vapor Phase from Solid Hydrogen Peroxide Compositions Samples of solid peroxohydrate or perborate-containing compositions, compositions 4-7 as set forth in Table 3, were placed in individual 66 liter polypropylene test chambers, maintained at 23° C., and 20% or 80% relative humidity. The pH values of these compositions are set forth in Table 4. The amounts of hydrogen peroxide concentrations in the vapor phase inside the test chambers were quantified over extended periods of time using a Draeger Pac III® gas monitor, fitted with a hydrogen peroxide sensor from Draeger Safety, Inc., Pittsburgh, Pa., USA. Hydrogen peroxide generated in the vapor phase is expressed in units of ppm and is set forth in Tables 5 and 6.

TABLE 3

Composition 4 = 10 grams sodium perborate monohydrate compound in open petri dish.
Composition 5 = 10 grams sodium percarbonate compound in open petri dish.
Composition 6 = 7.2 grams Peroxydone ® polyvinylpyrrolidone-hydrogen peroxide complex (22% hydrogen peroxide content), 12.8 grams sodium sulfate, combined solids contained within TYVEK ® pouch from DuPont Company, Wilmington, Delaware, USA.

TABLE 3-continued

Composition 7 = 4.8 grams urea-hydrogen peroxide complex (33% hydrogen peroxide content), 15.2 grams sodium sulfate, combined solids contained within TYVEK ® pouch from DuPont Company, Wilmington, Delaware, USA.

TABLE 4 pH Values For Solid Compositions 4-7, As 5% Solutions By Weight in Water

| Composition | pH of 5% solution, @ 23° C. |
|---|---|
| Composition 4 | 10.7 |
| Composition 5 | 10.5 |
| Composition 6 | 4.7 |
| Composition 7 | 5.7 |

TABLE 5

Generation Of Hydrogen Peroxide In The Vapor Phase From Solid Compositions 4-7 At 23° C. And 20% Relative Humidity

| Time (minutes) | Composition 4 | Composition 5 | Composition 6 | Composition 7 |
|---|---|---|---|---|
| 0 | 0.0 ppm | 0.0 ppm | 0.0 ppm | 0.0 ppm |
| 30 | 0.0 | 0.0 | 1.8 | 0.4 |
| 60 | 0.0 | 0.0 | 3.1 | 0.7 |
| 90 | 0.0 | 0.0 | 4.2 | 1.5 |
| 120 | 0.0 | 0.0 | 6.9 | 1.5 |
| 270 | 0.0 | 0.0 | 9.6 | 1.6 |

TABLE 6

Generation Of Hydrogen Peroxide In The Vapor Phase From Solid Compositions 4-7 At 23° C. And 80% Relative Humidity

| Time (minutes) | Composition 4 | Composition 5 | Composition 6 | Composition 7 |
|---|---|---|---|---|
| 0 | 0.0 ppm | 0.0 ppm | 0.0 ppm | 0.0 ppm |
| 60 | 0.0 | 0.0 | 11.2 | 1.5 |
| 180 | 0.0 | 0.0 | 14.5 | 3.1 |
| 3900 | 0.0 | 0.0 | 8.3 | 6.0 |

Thus, the data above illustrates the utility of solid acidic peroxohydrate compounds for the generation of hydrogen peroxide in the vapor phase. Peroxydone® and urea-hydrogen peroxide compounds effectively generate vapor phase hydrogen peroxide. Both are solid peroxohydrate compounds which produce acidic aqueous solutions. Sodium percarbonate, another solid peroxohydrate compound, does not generate hydrogen peroxide in the vapor phase. Aqueous solutions of sodium percarbonate are alkaline. Similarly, sodium perborate monohydrate, an alkaline borate salt containing complexed peroxo anion ($O_2^{2-}$), also does not generate vapor phase hydrogen peroxide. Thus, only solid compositions containing pH neutral to slightly acidic peroxohydrate compounds are effective generators of vapor phase hydrogen peroxide, and are thus employed in the solid deodorizing compositions of the present invention described herein.

EXAMPLE 3

Reduction of Tobacco Smoke Malodors from Fabric Using Vapor Phase Hydrogen Peroxide Generated and Passively Emitted from an Aqueous Liquid Composition Containing Hydrogen Peroxide Inside a 200 cu. ft. stainless steel chamber, held at 74° F. and 42% relative humidity, vapor phase hydrogen peroxide was generated and passively emitted from an 8% aqueous solution of hydrogen peroxide in water, identical to composition 1 (Table 1). 50 grams of 8% aqueous solution was evenly divided between two petri dishes, which were then placed on the floor of the chamber. The concentration of vapor phase hydrogen peroxide in the room was allowed to reach equilibrium (within 24 hours) and was measured as 1.3-1.5 ppm using a Draeger Pac III® gas monitor, fitted with a hydrogen peroxide sensor.

After the vapor phase hydrogen peroxide concentration reached an equilibrium value within the test chamber, two 8"×10" cotton cloth swatches, impregnated with tobacco smoke odor were suspended in the 200 cu. ft. chamber. The two petri dishes of 8% aqueous hydrogen peroxide remained in the chamber. The fabric swatches remained undisturbed in the 200 cu. ft. room for 24 hours.

After 24 hours, the test swatches were removed from the chamber. Each swatch was placed in a separate capped 1-gallon glass test jar for evaluation by a "sniff-test" malodor panel. "Sniff test" panelists rated the amount of tobacco smoke malodor present in each jar's headspace (scale=1-7; where 1=none at all, 7=large amount). Test swatches for clean cloth (not containing tobacco smoke odor) and cloth soiled with tobacco smoke odor but treated only with ambient air in an identical test chamber for 24 hours were also evaluated by the panelists. The tests were performed in triplicate. The resulting data demonstrated a significant reduction of tobacco smoke malodor for the smoke-treated test swatches exposed to an environment containing air including hydrogen peroxide in the vapor phase, relative to similarly treated swatches exposed only to ambient air as shown in Table 7.

TABLE 7

Reduction Of Tobacco Smoke Malodor For The Smoke-Treated Test Swatches Exposed To Vapor Phase Hydrogen Peroxide, Relative To Similar Control Swatches

| Test Cloth | Test 1: Average Result | Test 2: Average Result | Test 3: Average Result |
|---|---|---|---|
| Clean - No tobacco odor | 2.11 | 1.28 | 1.45 |
| Tobacco odor, ambient air treatment | 4.07 | 4.84 | 4.77 |
| Tobacco odor, vapor phase hydrogen peroxide treatment | 2.69 | 3.34 | 3.17 |

EXAMPLE 4

Analytical Measurement of Tobacco Smoke Malodor Component Reduction from Smoke-Treated Fabric Using Vapor Phase Hydrogen Peroxide Treatment of tobacco smoke impregnated cotton fabric with vapor phase hydrogen peroxide involved placing a 20 gram pouch of Composition 6 (Example 2), 1 gram of water on a paper blotter, and the smoke-treated fabric into a 1 gallon glass jar. A similar control sample consisted of the smoke treated fabric plus the water/blotter in a 1-gallon glass jar with ambient room air. The fabric was suspended from the lid of the jar. Static headspace samples were collected after 24 and 48 hours using solid phase microextraction (SPME, Supleco part #57326-U, Stableflex 65 μm thick film, PDMS-DVB). Gas chromatographic data was acquired using an Agilent 6890 GC equipped with a DB-1 glass capillary column and a nitrogen-phosphorous detector. Four of the major gas chromatography peaks (representing smoke malodor compounds) from the control sample were selected for comparison to identically eluted peaks resulting from the smoke-treated swatches exposed to vapor phase hydrogen peroxide. The percentage reduction of the peak area for each of the four peaks derived from the smoke-treated cloth exposed to air containing hydrogen peroxide in the vapor phase, relative to the peak areas for control smoke-treated cloths, was calculated for 24 and 48 hour treatment times. The results are presented in Table 8. Data is derived from samples prepared in triplicate.

TABLE 8

Smoke Treated Cloth Exposed To Vapor Phase Hydrogen Peroxide Compared To Control Cloth. Percent Peak Area Reduction For Tobacco Smoke Gas Phase Components, 24 And 48 Hours Exposure Times

| Exposure Time | Average Percent Peak Area Reduction Versus Control | | | |
|---|---|---|---|---|
| (Hrs) | Peak 1 | Peak 2 | Peak 3 | Peak 4 |
| 24 | 96 | 90 | 79 | 100 |
| 48 | 100 | 100 | 80 | 100 |

Thus, for the smoke odor soiled cloth exposed to vapor phase hydrogen peroxide in air, the analytical results show a large reduction in the gas phase concentration of the 4 smoke malodor components selected for evaluation, relative to the smoke-soiled cloths treated only with ambient air. The results of the study showed that vapor phase hydrogen peroxide treatment of smoke impregnated fabric reduced the level of the four malodor components collected from the vapor phase by 79 to 100% after 24 hours of exposure and 80 to 100% after 48 hours of exposure. Similar results were observed for other gas chromatography peaks for the smoke malodor soil not detailed here.

The "sniff test panel" results in Example 3 and the analytical results from Example 4 demonstrate the correlation between the perceived (olefactory) reduction in smoke malodor and the analytical quantification of malodor component reduction using compositions and methods of this invention.

Alternative embodiments of the invention employing pH neutral to mildly acidic liquid hydrogen peroxide compositions may also be effective for application towards the reduction or elimination of malodors from indoor air and surfaces in contact with the indoor air.

Although the present invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments described herein.

We claim:

1. A method of reducing malodors from air and/or surfaces in contact with said air within an indoor environment comprising providing said air with hydrogen peroxide in vapor phase generated by passive sublimation of hydrogen peroxide from a solid composition including at least one pH neutral to slightly acidic peroxohydrate compound.

2. The method according to claim 1 wherein said solid composition comprises about 0.1% to about 50% by weight hydrogen peroxide.

3. The method according to claim 1 wherein said solid composition comprises about 0.1% to about 10% by weight hydrogen peroxide.

4. The method according to claim 3 wherein said peroxohydrate compound comprises one or more of urea peroxohydrate, sodium sulfate peroxohydrate, and a peroxohydrate of poly(vinyl pyrrolidone) polymer.

5. The method according to claim 4 wherein said solid composition is a powder, granule, compressed tablet or crystalline solid form.

6. The method according to claim 5 wherein said solid composition further includes one or more of fragrances, colorants, surfactants, solvents, binders, processing agents and hydrogen peroxide-stabilizing agents.

7. The method according to claim 1 wherein the sublimation of the hydrogen peroxide is enhanced by heating or a fan.

8. A method of reducing malodors from air and/or surfaces in contact with said air within an indoor environment consisting of providing said air with hydrogen peroxide in vapor phase generated by passive sublimation of hydrogen peroxide from a solid composition including at least one pH neutral to slightly acidic peroxohydrate compound, and one or more of fragrances, colorants, surfactants, solvents, binders, processing agents and hydrogen peroxide-stabilizing agents; and wherein said hydrogen peroxide is about 0.1% to about 50% by weight of said solid composition.

9. The method according to claim 8 wherein said solid composition comprises about 0.1% to about 10% by weight hydrogen peroxide.

10. The method according to claim 9 wherein said peroxohydrate compound comprises one or more of urea peroxohydrate, sodium sulfate peroxohydrate, and a peroxohydrate of poly(vinyl pyrrolidone) polymer.

11. The method according to claim 10 wherein said solid composition is a powder, granule, compressed tablet or crystalline solid form.

12. The method according to claim 8 wherein the sublimation of the hydrogen peroxide is enhanced by heating or a fan.

\* \* \* \* \*